United States Patent
Xi et al.

(10) Patent No.: US 10,548,393 B2
(45) Date of Patent: Feb. 4, 2020

(54) TOOTHBRUSH WITH ENHANCED CLEANING EFFECTS

(71) Applicant: COLGATE-PALMOLIVE COMPANY, New York, NY (US)

(72) Inventors: Wen Jin Xi, Shanghai (CN); Guang Sheng Guo, Yangzhou (CN); Xiang Ji Ding, Yangzhou (CN)

(73) Assignee: Colgate-Palmolive Company, New York, NY (US)

( * ) Notice: Subject to any disclaimer, the term of this patent is extended or adjusted under 35 U.S.C. 154(b) by 290 days.

(21) Appl. No.: 15/507,329

(22) PCT Filed: Sep. 3, 2014

(86) PCT No.: PCT/CN2014/085796
§ 371 (c)(1),
(2) Date: Feb. 28, 2017

(87) PCT Pub. No.: WO2016/033745
PCT Pub. Date: Mar. 10, 2016

(65) Prior Publication Data
US 2017/0245627 A1    Aug. 31, 2017

(51) Int. Cl.
*A46B 9/04*    (2006.01)
*A46B 9/02*    (2006.01)
(Continued)

(52) U.S. Cl.
CPC .............. *A46B 9/04* (2013.01); *A46B 9/025* (2013.01); *A46B 9/028* (2013.01);
(Continued)

(58) Field of Classification Search
CPC .......... A46B 9/025; A46B 9/028; A46B 9/04; A61C 17/3481
(Continued)

(56) References Cited

U.S. PATENT DOCUMENTS 2,155,245 A    4/1939 Sekine
2,797,424 A    7/1957 Olson
(Continued)

FOREIGN PATENT DOCUMENTS

CN    101102698    1/2008
CN    101194784 A   6/2008
(Continued)

OTHER PUBLICATIONS

International Search Report and the Written Opinion of the International Searching Authority issued in international application PCT/CN2014/085796 dated Jun. 1, 2015.
(Continued)

*Primary Examiner* — Laura C Guidotti

(57) ABSTRACT

A toothbrush (100) having a combination of tapered and non-tapered cleaning elements (50) for enhanced cleaning effects and having a plurality of tapered bristle tufts of differing tuft configurations including, a first tapered bristle tuft (500) having a dome-shaped bristle tip profile (520) toward one end (210) of the head (200), a second tapered bristle tuft (602) having an arcuate-shaped bristle configuration (622) toward an opposite end (222) of the head (200), and a plurality of laterally-extending third tapered bristle tufts (600) arranged in an alternating fashion with non-tapered bristle tufts (630) and disposed between the first and second tapered bristle tufts (500, 602).

9 Claims, 3 Drawing Sheets

(51) Int. Cl.
*A46B 15/00* (2006.01)
*A61C 17/34* (2006.01)

(52) U.S. Cl.
CPC ...... *A46B 15/0081* (2013.01); *A61C 17/3481* (2013.01); *A46B 2200/1066* (2013.01)

(58) Field of Classification Search
USPC .......................................................... D4/104
See application file for complete search history.

(56) References Cited

U.S. PATENT DOCUMENTS

| | | | |
|---|---|---|---|
| 3,196,299 A * | 7/1965 | Kott | A61C 17/3481 310/81 |
| 4,864,676 A | 9/1989 | Schaiper | |
| 5,628,082 A | 5/1997 | Moskovich | |
| D403,510 S | 1/1999 | Menke et al. | |
| 6,308,367 B1 | 10/2001 | Beals et al. | |
| D454,252 S | 3/2002 | Lee | |
| 6,496,999 B1 | 12/2002 | Gleason et al. | |
| 6,546,586 B2 | 4/2003 | Cho | |
| D483,183 S | 12/2003 | De Salvo | |
| 6,735,804 B2 | 5/2004 | Carlucci et al. | |
| 7,386,905 B2 | 6/2008 | Eliav et al. | |
| 7,725,981 B2 | 6/2010 | Moskovich et al. | |
| 7,757,326 B2 | 7/2010 | Jimenez et al. | |
| 7,788,756 B2 | 9/2010 | Kraemer | |
| 7,832,042 B2 | 11/2010 | DePuydt et al. | |
| 8,166,601 B2 | 5/2012 | Brown, Jr. et al. | |
| 8,185,993 B2 * | 5/2012 | Fischer | A46D 1/0284 15/28 |
| 8,234,742 B2 | 8/2012 | Blaustein et al. | |
| 8,239,996 B2 * | 8/2012 | Garbers | A46D 1/00 15/167.1 |
| 8,332,982 B2 | 12/2012 | Braun et al. | |
| 8,341,792 B2 | 1/2013 | Fischer et al. | |
| 9,526,324 B2 | 12/2016 | Lee | |
| 2006/0026784 A1 | 2/2006 | Moskovich et al. | |
| 2006/0057087 A1 * | 3/2006 | Moskovich | A46B 5/0029 424/65 |
| 2006/0080799 A1 | 4/2006 | Lucente | |
| 2010/0180392 A1 | 7/2010 | Binet | |
| 2010/0223745 A1 * | 9/2010 | Kraemer | A46B 9/02 15/167.1 |
| 2010/0306941 A1 | 12/2010 | Erskine-Smith et al. | |
| 2011/0030160 A1 | 2/2011 | Knutzen | |
| 2011/0138559 A1 | 6/2011 | Plotka | |
| 2011/0146014 A1 | 6/2011 | Jimenez et al. | |
| 2011/0258794 A1 | 10/2011 | Headstrom et al. | |
| 2011/0308029 A1 * | 12/2011 | Edelstein | A46B 5/026 15/167.1 |
| 2013/0139339 A1 | 6/2013 | Hess | |
| 2013/0326833 A1 | 12/2013 | Varila | |

FOREIGN PATENT DOCUMENTS

| | | |
|---|---|---|
| CN | 100401940 | 7/2008 |
| CN | 201356213 | 12/2009 |
| JP | 2013081738 | 5/2013 |
| WO | WO2001012013 A1 | 2/2001 |
| WO | WO200143585 A1 | 6/2001 |
| WO | 2006/055572 | 5/2006 |
| WO | WO2011070549 A1 | 6/2011 |

OTHER PUBLICATIONS

LMFAO Singing Toothbrush by Brushbuddies accessed from http://www.brushbuddies.com/lmfao-singing-sexy-and-i-know-it-party-rock-anthem-category.html#.U1quNa7D_cs on Apr. 7, 2014.

* cited by examiner

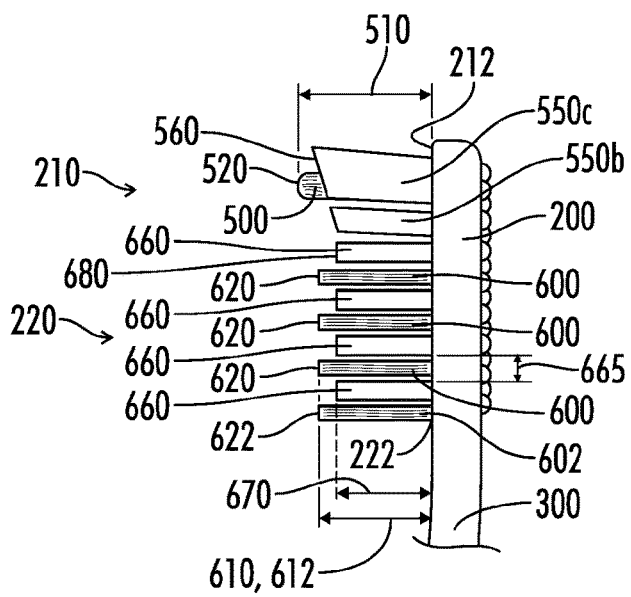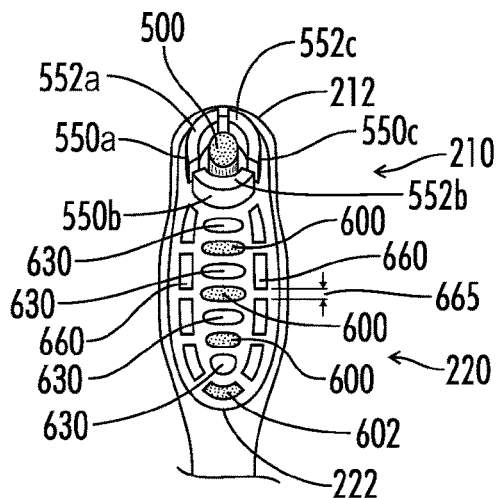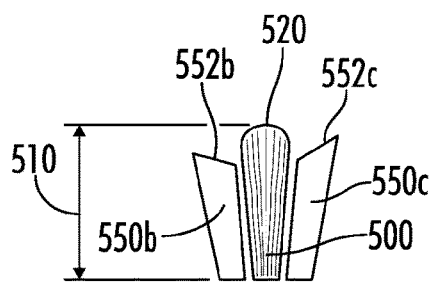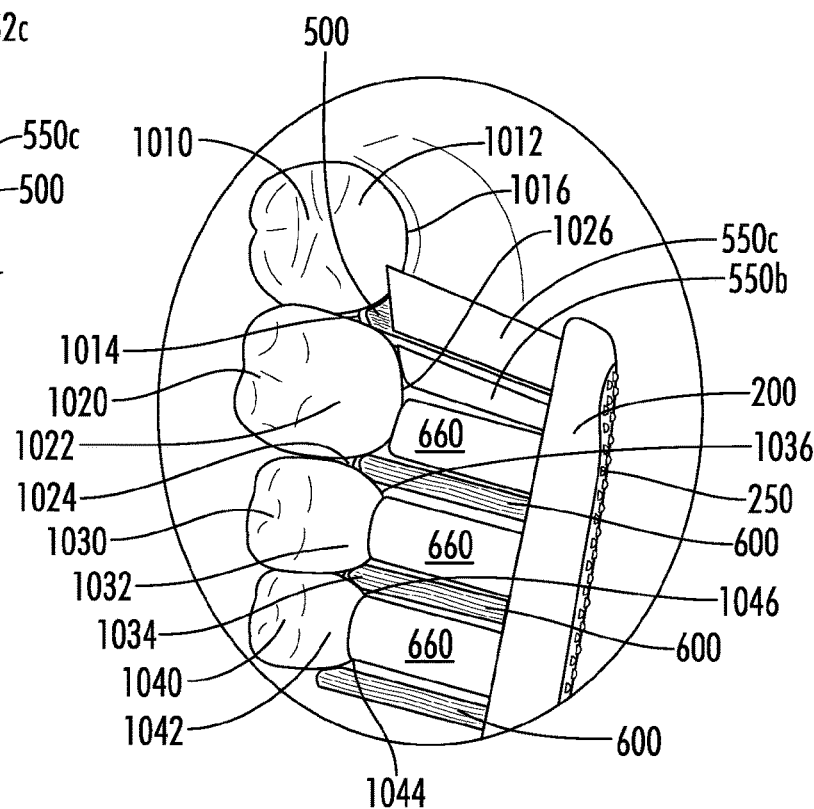
FIG. 4
FIG. 5
FIG. 6
FIG. 7

TOOTHBRUSH WITH ENHANCED CLEANING EFFECTS

BACKGROUND

Tapered bristles with thinner bristle tips or tip regions are particularly known for efficacy in reaching the interproximal spaces in-between teeth, at the gingival margin and in the subgingival access. Traditional non-tapered bristles are generally known to be effective along wider tooth surfaces, such as the facial, buccal, lingual, and occlusal surfaces. What is needed is a more effective arrangement of bristles for efficient simultaneous cleaning of the tooth surfaces as well as the interproximal and gingival areas of the oral cavity.

BRIEF SUMMARY

There is provided a toothbrush having a combination of tapered and non-tapered cleaning elements for enhanced cleaning effects. More specifically, in one embodiment there is provided a plurality of tapered bristle tufts of differing tuft configurations including a first tapered bristle tuft having a dome-shaped bristle tip profile situated toward one end of the head, a second tapered bristle tuft having an arcuate-shaped configuration situated toward an opposite end of the head, and a plurality of laterally-extending third tapered bristle tufts arranged in an alternating fashion with non-tapered bristle tufts and disposed between the first and second tapered bristle tufts. The tapered bristle tufts are preferably longer than the non-tapered bristle tufts to provide interdental penetration and more efficient and effective interdental and gingival cleaning. In one embodiment, the first tapered bristle tuft is preferably surrounded by a cup-shaped bristle tuft that covers and cleans the outer surfaces of a tooth. Additional non-tapered bristles are situated on the head to provide targeted cleaning of outer wider teeth surfaces.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 4 is an enlarged view of the toothbrush head of FIG. 1;

FIG. 5 is an enlarged view of the toothbrush head of FIG. 2;

FIG. 6 is a diagrammatic view taken along line 6-6 of FIG. 2;

FIG. 7 illustrates one embodiment of a toothbrush of the present disclosure in use;

DETAILED DESCRIPTION

Figure 1:
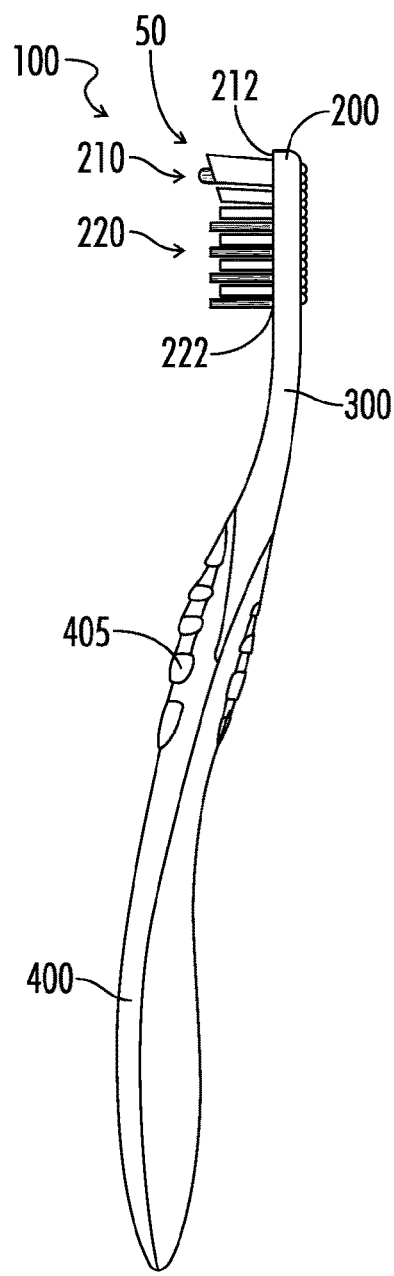
FIG. 1 is a side view of one embodiment of a toothbrush in accordance with the present disclosure.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "proximal," "distal," "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the preferred embodiments. Accordingly, the invention expressly should not be limited to such preferred embodiments illustrating some possible non-limiting combination of features that may exist alone or in other combinations of features; the scope of the invention being defined by the claims appended hereto.

Figure 2:
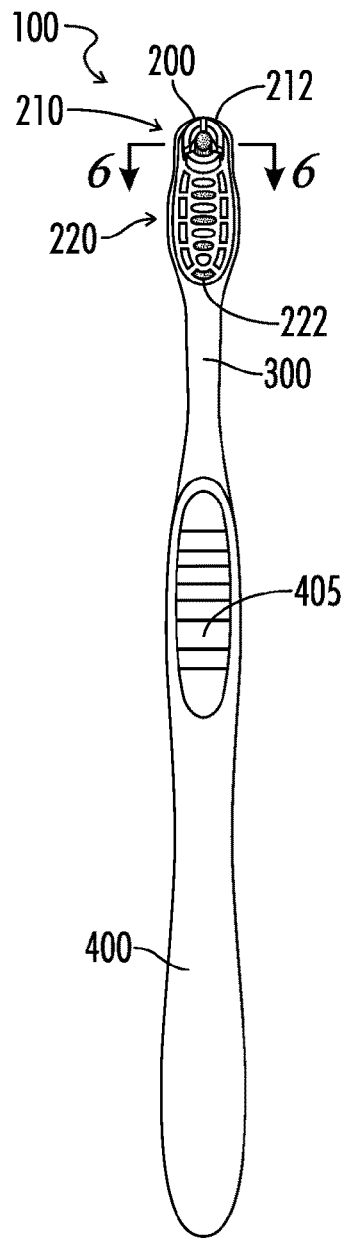
FIG. 2 is a front view thereof.
Figure 3:
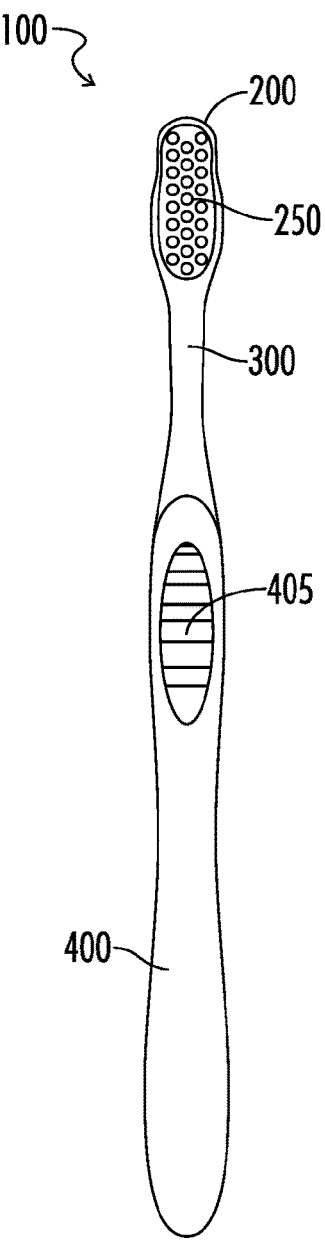
FIG. 3 is a rear view thereof.

FIG. 1 is a side view, FIG. 2 is a front view and FIG. 3 is a rear view of one embodiment of a toothbrush 100 comprising a head 200 with cleaning elements 50, handle 400 and a neck 300 defined between the head 200 and handle 400. While the toothbrush 100 of the embodiments of FIGS. 1-8 is illustrated as a manual toothbrush having a certain handle configuration and shape, and including in the present embodiment a thumb grip 405 for example, it will be understood that such configuration and shape are not meant to be limiting, but that other configurations and shapes are possible. For example, a powered embodiment is illustrated in FIGS. 9-10, although again such powered embodiment illustrates a constructional configuration that is not meant to be limiting, and other configurations are possible, such as a combination of manual and powered or an enhanced manual brush. Further, the head, neck and handle may be manufactured from any material or combination of materials. The cleaning elements 50 described herein will generally be described as bristle tufts, although it will be understood that other types of cleaning elements may be used alone or in combination, including traditional bristle tufts, tapered bristle tufts and combinations of tapered and non-tapered tufts as well as combination tufts, combination bristles, cup-shaped bristle tuft configurations, wavy profiles, diagonally-oriented bristle tufts, zig-zag or sawtooth profiles, squeegee or wiper elements, and others. The head 200 may also be provided with other cleaning features that target the oral cavity, such as a tongue cleaner, gum massager, interdental pick, and the like. In addition, toothbrush 100 can be manual, powered or otherwise, it being understood that the present description is not to be limited to any one particular type of toothbrush or oral cleaning implement. This disclosure is not intended to be limited to any particular type of bristle attachment now known, such as stapled, in-mold tufting (IMT), anchor-free tufting (AFT) or combinations of the same, or hereinafter developed.

The head 200 further comprises a distal head region 210 with a distal tip 212, a proximal head region 220 with a proximal tip 222, a front surface 230 from which cleaning elements 50 extend, and a rear surface 240 that is optionally provided with a tissue cleaner 250 such as a tongue cleaner 250 or the like. While the illustrated tissue cleaner 250 is defined by a plurality of protrusions, it will be appreciated that other structural configurations are possible other than the illustrated spherical protrusions.

One embodiment of the cleaning elements 50 are detailed in FIGS. 4-6, which are close-up views of the head 200 and certain cleaning elements of the toothbrush 100 of FIGS. 1 and 2. The distal head region 210 further comprises a first distal bristle tuft 500 having a height 510 and a bristle tip profile 520. The first distal bristle tuft 500 is preferably formed from tapered bristles and has a rounded or dome-shaped bristle tip profile 520. The first distal bristle tuft 500 may extend at an angle from the front surface 230 of the head region 220, such as for example, at an acute angle toward the distal tip 212. The first distal tuft 500 is preferably at least partially surrounded by at least one additional second distal bristle tuft 550 having a cup-shaped configuration. When viewed from the side, the at least one additional second distal bristle tuft 550 may have an angled bristle tip profile 560 (FIG. 4) that is highest adjacent the distal tip 212 to engage the deeper areas of the oral cavity such as around the distal and lingual surfaces of the molars, for example. In the current embodiment, the second distal bristle tuft 550 is split into a plurality of sub-tufts 550a-c that surround the first distal tuft 500 to define the cup-shaped configuration (FIG. 5). Each sub-tuft 550a-c preferably includes an angled bristle tip profile 552a-552c as partially shown in FIG. 6. Each angled bristle tip profile 552a-c is angled away from the first distal tuft 500 such that the tips of the radially outermost bristles in each sub-tuft 550a-c extend further from the front surface 230 of the head 200 than the tips of the radially innermost bristles in each sub-tuft 552-a-c.

The proximal head region 220 preferably further comprises a plurality of laterally-arranged first proximal bristle tufts 600 having a height 610, as shown in FIG. 4, the tufts 600 preferably formed from tapered bristles and extending normal to the front surface 230 of the head 200. Each of the plurality of laterally-arranged first proximal bristle tufts 600 may have a substantially flat bristle tip profile 620 (FIG. 4) and an oval-shaped configuration, as shown in FIG. 5. The plurality of first proximal bristle tufts 600 preferably alternate, along a central longitudinal axis of the proximal head region 220, with a plurality of laterally-arranged second proximal bristle tufts 630 positioned adjacent the first proximal bristle tufts 600. The first proximal bristle tufts 600 are preferably formed from tapered bristles and have a height 610 that is preferably greater than a height 670 of the second proximal bristle tufts 630, which are preferably formed from non-tapered bristles.

In the present embodiment, there is also provided a plurality of third substantially longitudinally-arranged proximal bristle tufts 660 also having a height 670 and a substantially flat bristle tip profile 680. Collectively, the substantially longitudinally-arranged proximal bristle tufts 660 at least partially surround the first and second proximal bristle tufts 600, 630 and are arranged around the periphery of the proximal head region 220. The height of the second proximal bristle tufts 630 may be identical to the height 670 of the third proximal bristle tufts 660, and distinct from the height 610 of the first proximal bristle tufts 600. The third proximal bristle tufts 660 are preferably spaced in a staggered relation relative to the first and second proximal bristle tufts 600, 630 such that the first proximal bristle tufts 600 are situated along the central axis of the head 200 between the openings 665 defined by the third proximal bristle tufts 660 as shown in FIG. 5. Thus, as illustrated below, the first proximal bristle tufts 600 are able to target interdental regions of the oral cavity while the second and third proximal bristle tufts 630, 660 concurrently target larger tooth surfaces (e.g., buccal, lingual, occlusal), with the staggered arrangement of the first, second and third proximal bristle tufts preventing the different bristle tufts from concurrently conflicting or targeting the same space.

In the embodiment of FIGS. 1-6, there is also provided a fourth proximal bristle tuft 602 situated adjacent the proximal tip 222 of the head 200. The fourth proximal bristle tuft 602 has a height 612 and an arcuate bristle tuft configuration 622. The fourth proximal bristle tuft 602 is preferably formed from tapered bristles that are higher than the adjacent third proximal bristle tufts 660 so that the fourth proximal bristle tuft 602 compliments the first distal bristle tuft 500 and the first proximal bristle tuft 600 to provide tapered bristle coverage and interdental cleaning along the entirety of the head 200 from the first distal bristle tuft 500 at the distal tip 212 to the fourth proximal bristle stuff 602 at the proximal tip 222. Alternatively, the fourth proximal bristle tuft 602 may be formed from non-tapered bristles and be configured similar to adjacent third proximal bristle tufts 660, and having a similar height 670. The arcuate bristle tip configuration of the fourth proximal bristle tuft 602 is particularly effective in accessing and covering the gingival and subgingival regions that are often similarly arcuately contoured.

Thus, there is provided a toothbrush 100 having a combination of tapered and non-tapered cleaning elements for enhanced cleaning effects defined by, in the embodiment of FIGS. 1-6, a tapered cleaning element 500 adjacent the distal end 212 having a bristle tip profile 520 surrounded by one or more sub-tufts 550a-c in a cup-shaped configuration with each sub-tuft being provided with a bristle tip profile 552a-c. A tapered cleaning element 602 is provided adjacent the proximal end 222 having a bristle tip profile 622 that is different than the bristle tip profiles 552a-c. The bristle configurations 552a-c, 622 are primarily curved or arcuate. A plurality of tapered cleaning elements 600 is provided, each having a primarily non-curved bristle configuration 620 that is different than the primarily curved bristle configurations 552a-c, 622. The plurality of tapered cleaning elements 600 being disposed between the tapered cleaning elements 500 and 602. The tapered cleaning elements 500, 602 and 600 are coaxially aligned along a central axis of the toothbrush head 200 and respectively define a dome-shaped bristle tip profile 520, an arcuate bristle configuration with a rectangular profile 622, and a rounded or oval bristle configuration with a rectangular profile 620. In this embodiment, there is also provided a plurality of non-tapered cleaning elements 630, 660 surrounding the plurality of laterally-arranged tapered cleaning elements 600. The tuft configurations illustrated in the present embodiments are a non-limiting example of an arrangement of combinations of tapered and non-tapered cleaning elements that provide an efficient and efficacious cleaning of the oral cavity.

Figure 8:
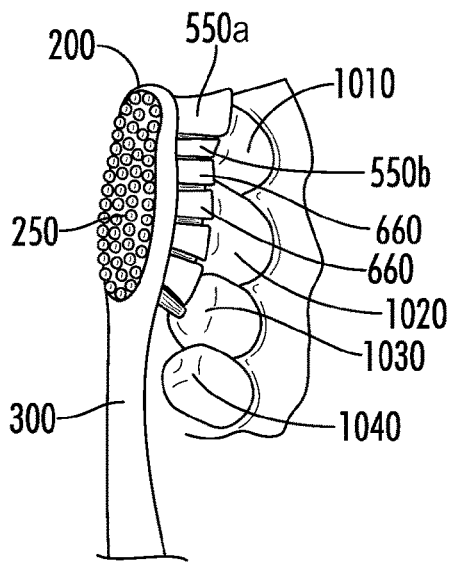
FIG. 8 illustrates one embodiment of a toothbrush of the present disclosure in use.

FIG. 7 illustrates one embodiment of a toothbrush 100 applied in an oral cavity against teeth 1010, 1020, 1030, 1040 (collectively teeth 1000) with respective outer surfaces 1012, 1022, 1032, 1042, respective interdental areas 1014, 1024, 1034, 1044, and respective gingival areas 1016, 1026, 1036, 1046. Each of the various tufts of cleaning elements target a different region of the teeth 1000 that collectively and efficiently clean the oral cavity with each brush stroke. For example, the bristle tip configuration 520 of the first distal bristle tuft 500 is, by virtue of being both tapered and higher than the second distal bristle tuft 550, adapted to reach into the interdental area and gingival areas 1014, 1016 in between teeth 1010 and 1020 of FIG. 7, and the use of tapered bristles on the first distal bristle tuft 500 provides for a floss-like interdental cleaning between such teeth 1010 and 1020. Similarly, the first proximal bristle tufts 600, by virtue of being both tapered and higher than the second and third proximal bristle tufts 630, 660 can concurrently target the interdental areas 1024, 1034 in-between teeth 1020 and 1030 and in between teeth 1030 and 1040 as shown in FIG. 7. Meanwhile, the second distal bristle tuft 550, as well as the second and third proximal bristle tufts 630, 660, which are collectively preferably not tapered and shorter than the first distal and proximal bristle tufts 500, 600, can provide efficient and effective cleaning to the outer surfaces of the teeth 1000. In addition, as shown in FIG. 8, the cup-shaped arrangement of the sub-tufts 550a-c of the second distal bristle tuft 550 is particularly suited to surround and clean the outer surfaces 1012 and gingival areas 1016 of the tooth 1010. Thus, the single application of the toothbrush 100 in an oral cavity results in the simultaneous cleaning of a plurality of interdental and gingival areas and various teeth surfaces, and also soft tissue surfaces through the engagement of tissue cleaner 250 (FIG. 3).

Figure 9:
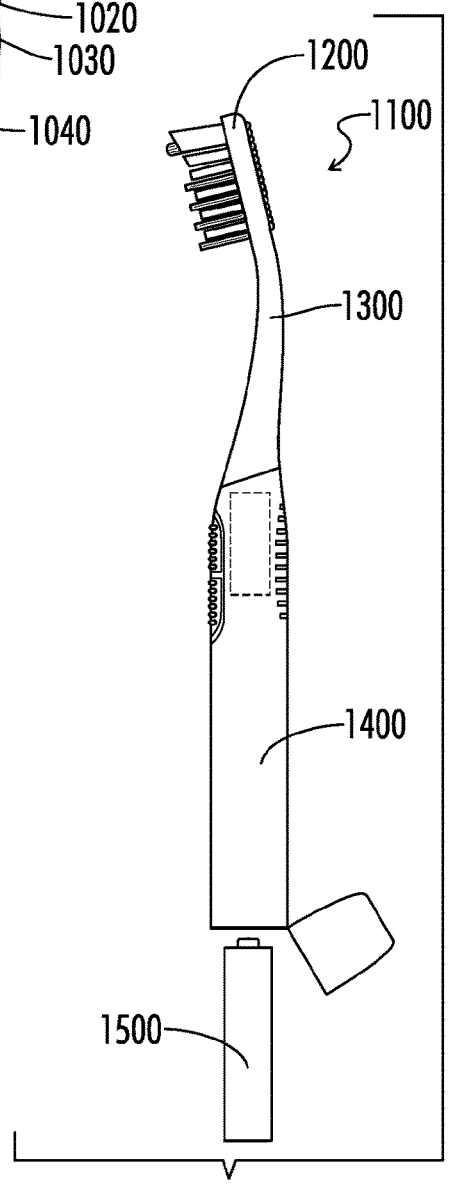
FIG. 9 is a side view of an alternative embodiment of a powered toothbrush in accordance with the present disclosure.
Figure 10:
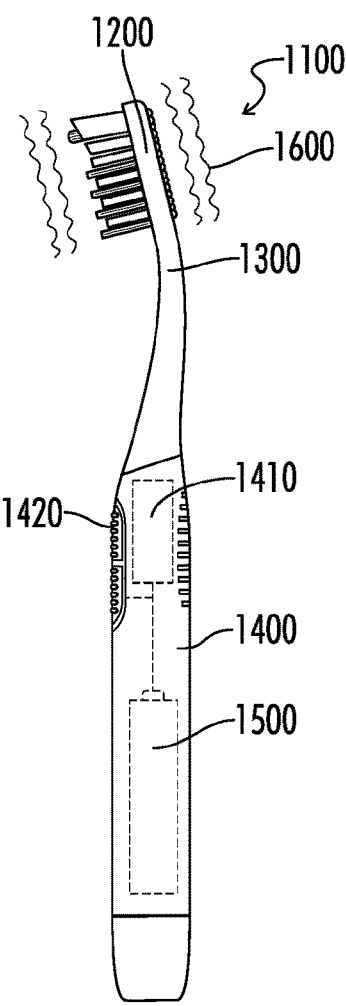
FIG. 10 illustrates the toothbrush of FIG. 9 in a powered state.

FIGS. 9-10 illustrate one embodiment of a powered version a toothbrush 1100 comprising a head 1200 having the same bristle configuration as the head 200 of the previously discussed embodiment, handle 1400 and a neck 1300 defined between the head 1200 and handle 1400. The handle 1400 preferably further comprises a removable power source 1500, such as a battery, that powers a vibration structure 1410, such as an eccentric, that is activated by a switch 1420 on the surface 1430 of the handle 1400. The vibration structure 1410 may be situated in the handle 1400 as illustrated, or in the neck 1300, or adjacent the neck 1300 or the handle 1400, or it may even be situated in the head 1200. While a removable power source 1500 is shown and described, it will be appreciated that a non-removable power source or other type of power source can be used if desired. The vibration structure 1410 causes the neck 1300 and the head 1200 to vibrate 1600 relative to the handle 1400 to provide a more effective and more efficient cleaning of the oral cavity through sonic friction. The frequency of vibration 1600 can vary and can optionally be adjusted through a vibration adjustment switch (not shown) provided on the handle or elsewhere if it is desired to adjust the vibration due to teeth and gum sensitivities or the like, or to create a more aggressive cleaning if desired.

Referring back to FIG. 7, with a powered version of a toothbrush 1100 applied to the teeth 1000 as shown, the vibration in the head preferably creates an enhanced cleaning through the vibratory contact of the longer tapered bristles within the interdental areas 1014, 1024, 1034, 1044 and gingival areas 1016, 1026, 1036, 1046 and the concurrent vibratory contact of the shorter non-tapered bristles along adjacent teeth outer surfaces. The vibratory engagement of the tapered bristles further results in a floss-like movement where the tapered bristles pulse into and out of the targeted cleaning areas similar to the manner in which floss is manually engaged along tooth surfaces and interdental and gingival areas, thus creating a more efficient movement and cleaning result. Referring back to FIG. 8, with a powered version of a toothbrush 1100, the cup-shaped sub-tufts 550a-c of the second distal bristle tuft 550 pulse and vibrate both into and around the outer surfaces, interdental and gingival regions for enhanced cleaning of such areas, while adjacent tapered and non-tapered cleaning elements address similar tooth regions as discussed in connection with FIG. 8, but with greater efficiency and efficacy through the vibratory motion.

While the powered embodiment of FIGS. 9-10 illustrate the same head configuration as the manual embodiment of FIGS. 1-8, it will be appreciated that a different or varied head configuration can be used without departing from the scope of the present disclosure. Also, while FIGS. 9-10 illustrate a different handle configuration 1400 as compared with the handle 400 of FIGS. 1-8, it will be appreciated that a powered version could also incorporate the handle configuration 200 of FIGS. 1-8, or a different handle configuration as desired.

FIGS. 1-10 illustrate one possible arrangement and layout of cleaning elements of various shapes, configurations, constructions and cleaning profiles. This arrangement is not meant to be limiting, as the cleaning elements could be re-arranged or re-organized without departing from the scope of the present disclosure. For example, while the first distal bristle tuft 500 having a dome-shaped bristle tip configuration 520 is situated adjacent the distal end 212, such tuft could also be situated elsewhere on the toothbrush head 200, or there could be multiple tufts 500 having similar bristle tip configurations 520 positioned at strategic locations along the head 200. Other tuft arrangements are possible.

What is claimed is:

1. A toothbrush comprising:
   a head and a neck, the head having a distal tip, a proximal head region adjacent the neck, and a distal head region adjacent the distal tip;
   the distal head region further comprising a first distal bristle tuft at least partially surrounded by at least one second distal bristle tuft, a tip of the first distal bristle tuft being further away from the head than a tip of the at least one second bristle tuft, wherein the first distal bristle tuft further comprises tapered bristles;
   a plurality of first proximal bristle tufts and a plurality of second proximal bristle tufts adjacent the first proximal bristle tufts, a tip of each first proximal bristle tufts being further away from the head than a tip of at least one adjacent second proximal bristle tuft; and
   a plurality of laterally-arranged first proximal bristle tufts and a plurality of laterally-arranged second proximal bristle tufts;
   wherein the first and second proximal bristle tufts are arranged in an alternating fashion;
   wherein the proximal head region further comprises a plurality of third proximal bristle tufts at least partially surrounding the first and second proximal bristle tufts, the second and third proximal bristle tufts each have a rectangular shape; and
   wherein the second proximal bristle tufts and the at least one second distal bristle tuft are non-tapered.

2. The toothbrush of claim 1, wherein the first distal bristle tuft has a first distal bristle tip profile, and wherein the first proximal bristle tuft further comprises tapered bristles having a first proximal bristle tip profile that differs from the first distal bristle tip profile.

3. The toothbrush of claim 1, wherein the at least one second distal bristle tuft is split into a plurality of second distal bristle sub-tufts each defining a cleaning surface that is angled relative to the first distal bristle tuft.

4. The toothbrush of claim 3, wherein each cleaning surface is angled away from the first distal bristle tuft.

5. The toothbrush of claim 1, further comprising a tissue cleaner on a rear surface of the head.

6. The toothbrush of claim 1, further comprising a vibrating head.

7. The toothbrush of claim 6, further comprising a handle and a removable power source in the handle that imparts vibrations in the head.

8. A toothbrush comprising:
a head and a neck, the head having a distal tip, a proximal head region adjacent the neck, and a distal head region adjacent the distal tip;
the distal head region further comprising a first distal bristle tuft at least partially surrounded by at least one second distal bristle tuft, a tip of the first distal bristle tuft being further away from the head than a tip of the at least one second bristle tuft, wherein the first distal bristle tuft further comprises tapered bristles;
a plurality of first proximal bristle tufts and a plurality of second proximal bristle tufts adjacent the first proximal bristle tufts, a tip of each first proximal bristle tufts being further away from the head than a tip of at least one adjacent second proximal bristle tuft; and
a plurality of laterally-arranged first proximal bristle tufts and a plurality of laterally-arranged second proximal bristle tufts;
wherein the first and second proximal bristle tufts are arranged in an alternating fashion;
wherein the proximal head region further comprises a plurality of third proximal bristle tufts at least partially surrounding the first and second proximal bristle tufts; and
wherein the second proximal bristle tufts and the at least one second distal bristle tuft are non-tapered; and
a fourth proximal bristle tuft adjacent the neck and formed from tapered bristles and having an arcuate bristle configuration.

9. A toothbrush comprising:
a head and a neck, the head having a distal tip, a proximal head region adjacent the neck, and a distal head region adjacent the distal tip;
the distal head region further comprising a first distal bristle tuft at least partially surrounded by at least one second distal bristle tuft, a tip of the first distal bristle tuft being further away from the head than a tip of the at least one second bristle tuft, wherein the first distal bristle tuft further comprises tapered bristles;
a plurality of first proximal bristle tufts and a plurality of second proximal bristle tufts adjacent the first proximal bristle tufts, a tip of each first proximal bristle tufts being further away from the head than a tip of at least one adjacent second proximal bristle tuft;
a plurality of third proximal bristle tufts at least partially surrounding the first and second proximal bristle tufts;
a fourth proximal bristle tuft adjacent the neck and formed from tapered bristles and having an arcuate bristle configuration;
wherein the fourth proximal bristle tuft is higher than and situated in between two adjacent third proximal bristle tufts.

* * * * *